(12) United States Patent
Krusenklaus

(10) Patent No.: US 6,780,163 B1
(45) Date of Patent: Aug. 24, 2004

(54) STRAP SYSTEM FOR TREATING SHIN PAIN

(76) Inventor: John H. Krusenklaus, 7260 Brickey La., Knoxville, TN (US) 37918

( * ) Notice: Subject to any disclaimer, the term of this patent is extended or adjusted under 35 U.S.C. 154(b) by 0 days.

(21) Appl. No.: 10/345,742

(22) Filed: Jan. 16, 2003

Related U.S. Application Data

(63) Continuation of application No. 10/191,858, filed on Jul. 9, 2002, now abandoned, which is a continuation of application No. 09/794,558, filed on Feb. 27, 2001, now abandoned.

(51) Int. Cl.[7] .................................................. A61F 5/00
(52) U.S. Cl. ....................................................... 602/62
(58) Field of Search .............................. 602/19, 23, 5, 602/20, 26, 60–63, 65, 75; 128/882; 2/22, 911

(56) References Cited

U.S. PATENT DOCUMENTS

| | | | | |
|---|---|---|---|---|
| 3,463,147 A | * | 8/1969 | Stubbs | 602/20 |
| 3,473,527 A | * | 10/1969 | Spiro | 602/26 |
| 3,804,084 A | * | 4/1974 | Lehman | 602/26 |
| 3,935,858 A | * | 2/1976 | Harroff | 602/26 |
| 4,294,238 A | | 10/1981 | Woodford | |
| 4,372,297 A | * | 2/1983 | Perlin | 601/151 |
| 4,700,406 A | | 10/1987 | Meistrell | |
| 5,086,761 A | * | 2/1992 | Ingram | 602/26 |
| 5,307,521 A | * | 5/1994 | Davis | 2/22 |
| 5,405,312 A | | 4/1995 | Jacobs | |
| 5,472,413 A | * | 12/1995 | Detty | 602/26 |
| 5,513,658 A | * | 5/1996 | Goseki | 128/882 |
| 5,556,374 A | * | 9/1996 | Grace et al. | 602/26 |
| 5,570,470 A | | 11/1996 | Miller | |
| 5,626,557 A | * | 5/1997 | Mann | 602/26 |
| 5,759,167 A | * | 6/1998 | Shields et al. | 602/26 |
| 5,795,312 A | * | 8/1998 | Dye | 601/151 |

* cited by examiner

*Primary Examiner*—Nicholas D. Lucchesi
*Assistant Examiner*—Huong Q. Pham
(74) *Attorney, Agent, or Firm*—Luedeka Neely & Graham PC

(57) ABSTRACT

A device for treating pain in a shin of a user, including a first substantially elastic strap member having a pair of opposite ends and an inner and outer surface and conformable to be wrapped in a state of tension around the shin of the user and securable in the state of tension and wrapped configuration by a first fastener operatively associated with one of the ends of the first strap member, a second substantially elastic strap member having a first end securable adjacent the outer surface of the first strap member and a plurality of fingers extending outwardly from the first end and conformable to be tensioned about the outer surface of the first strap member, and one or more second fasteners for securing the tensioned fingers to the outer surface of the first strap member.

5 Claims, 5 Drawing Sheets

(2 of 5 Drawing Sheet(s) Filed in Color)

STRAP SYSTEM FOR TREATING SHIN PAIN

CROSS-REFERENCE TO RELATED APPLICATION

This application is a continuation of application Ser. No. 10/191,858, filed Jul. 9, 2002, and entitled STRAP SYSTEM FOR TREATING SHIN PAIN now abandoned, which is a continuation of application Ser. No. 09/794,558, filed Feb. 27, 2001, and entitled STRAP SYSTEM FOR TREATING SHIN PAIN (abandoned).

FIELD OF THE INVENTION

The present invention relates to orthotic devices. More particularly, the invention relates to devices for treating shin pain.

BACKGROUND AND SUMMARY OF THE INVENTION

Shin splints are a type of shin pain common to runners. Shin splints are often treated by applying tape to the shins in a desired manner. Taping is inconvenient, loosens over time and loses its effectiveness and the tape is discarded after each use. Also, once the tape is applied, it cannot readily be adjusted in terms of position or tension.

Accordingly it is an object of the present invention to provide a device for treating shin pain.

Another object of the invention is to provide a device of the character described that is re-usable.

Still another object of the invention is to provide a device of the character described that is adjustable.

A further object of the invention is to provide a device of the character described that is economical to produce and uncomplicated in configuration.

With regard to the foregoing and other objects, the present invention is directed to a device for treating shin pain.

In a preferred embodiment, the device includes first and second substantially elastic strap members. The first strap member has a pair of opposite ends and an inner and outer surface and is conformable to be wrapped in a state of tension around the shin of the user. A first fastener associated with one of the ends of the first strap member is provided for securing the first strap member in the state of tension and wrapped configuration.

The second elastic strap member has a first end secureable adjacent the outer surface of the first strap member and a plurality of fingers extending outwardly from the first end and is conformable to be tensioned about the outer surface of the first strap member. One or more second fasteners are provided for securing the tensioned fingers to the outer surface of the first strap member.

In another aspect of the invention, there is provided a method for treating shin pain. In a preferred embodiment, the first strap member is wrapped around the shin in a tensioned state and secured to the first strap member by the first strap member. The second strap member is secured to the outer surface of the first strap member and the fingers tensioned and secured to the outer surface of the first strap member by the second fasteners.

BRIEF DESCRIPTION OF THE DRAWINGS

The claim of this patent contains at least one drawing executed in color. Copies of this patent with color drawings will be provided by the Patent and Trademark Office upon request and payment of the necessary fee.

Further advantages of the invention will become apparent by reference to the detailed description of preferred embodiments when considered in conjunction with the figures, which are not to scale, wherein like reference numbers, indicate like elements through the several views, and wherein.

DETAILED DESCRIPTION

Figure 1:
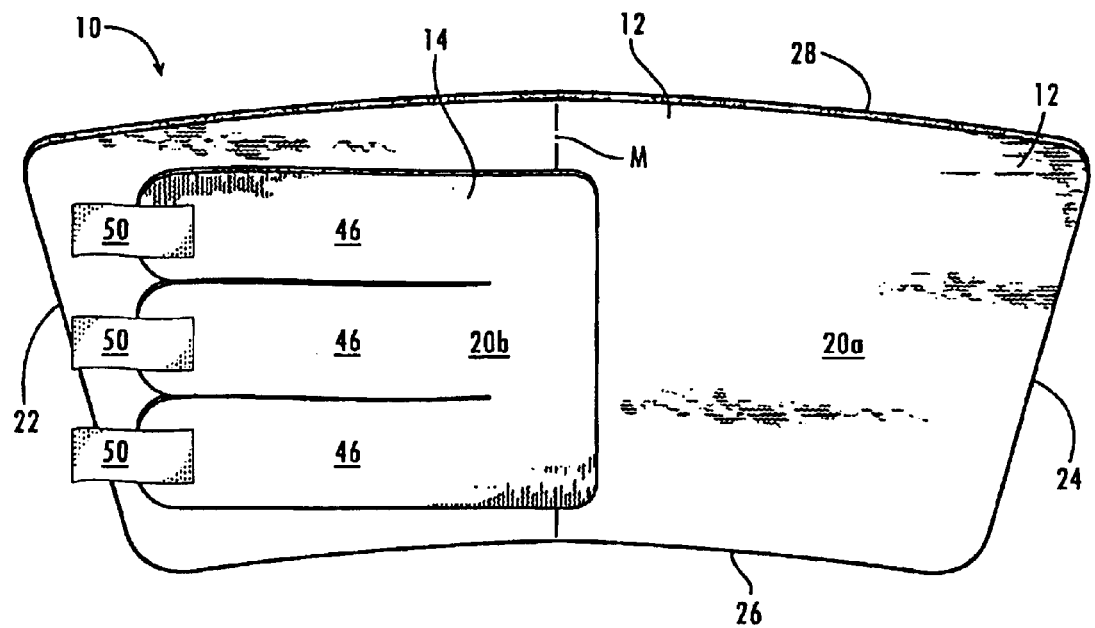
FIG. 1 is a plan view of a strap system in accordance with a preferred embodiment of the invention and FIG. 1a is a cross-sectional view of a strap member of the system of FIG. 1.

With initial reference to FIG. 1, the invention relates to a strap system 10 that is particularly suitable for providing comfort for painful shin conditions such as shin splints (medial tibia stress syndrome). The strap system 10 includes a primary strap member 12 and a secondary strap member 14 attached to the primary strap member 12.

Figure 1A:
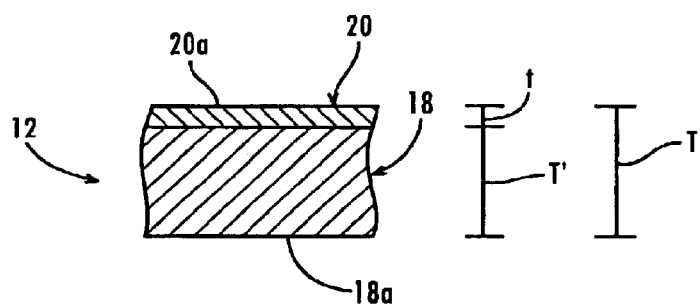
Figure 2:
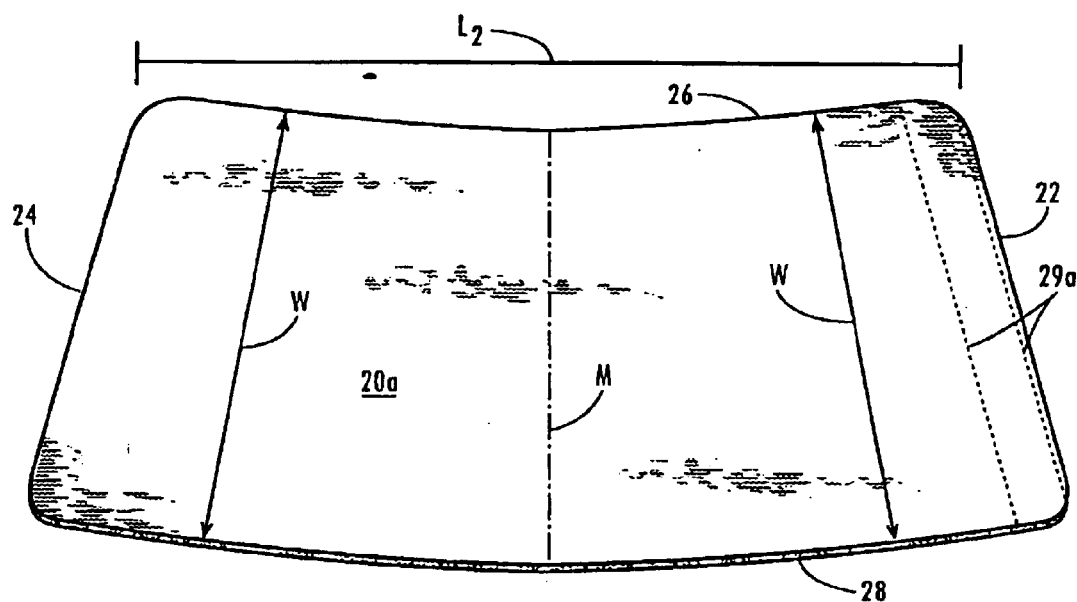
FIG. 2 is a front plan view of a primary strap member of the strap system of FIG. 1.
Figure 3:
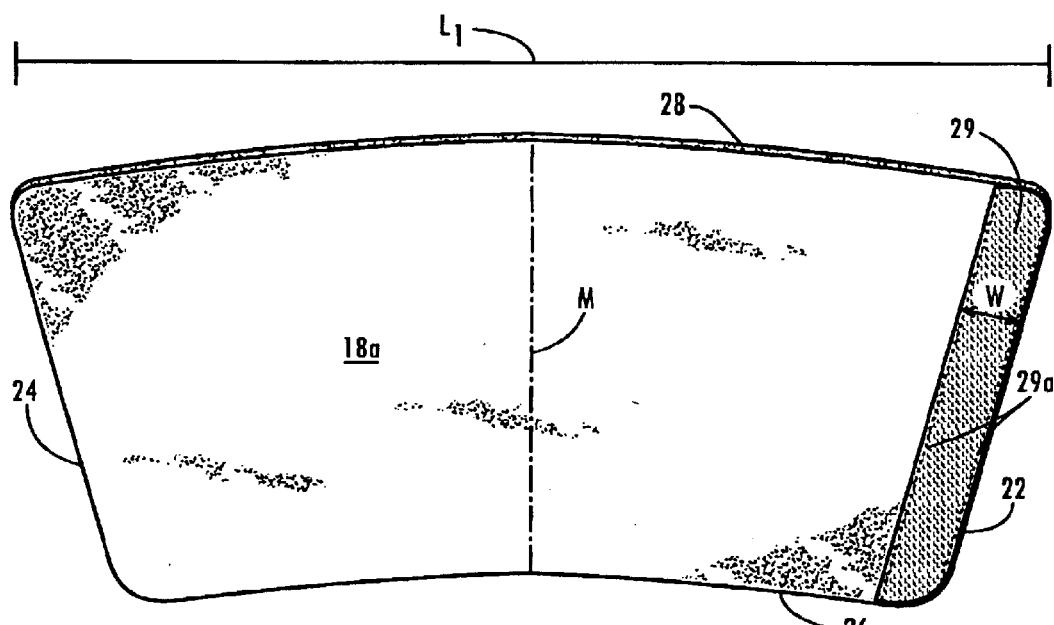
FIG. 3 is a rear plan view of the primary strap member of FIG. 2.
Figure 4:
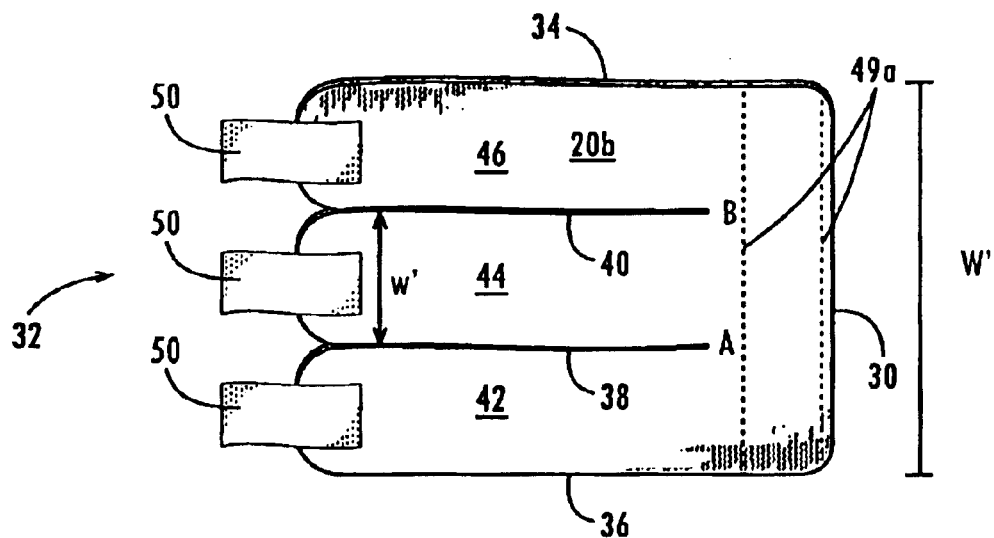
FIG. 4 is a front plan view of a secondary strap member of the strap system of FIG. 1.
Figure 5:
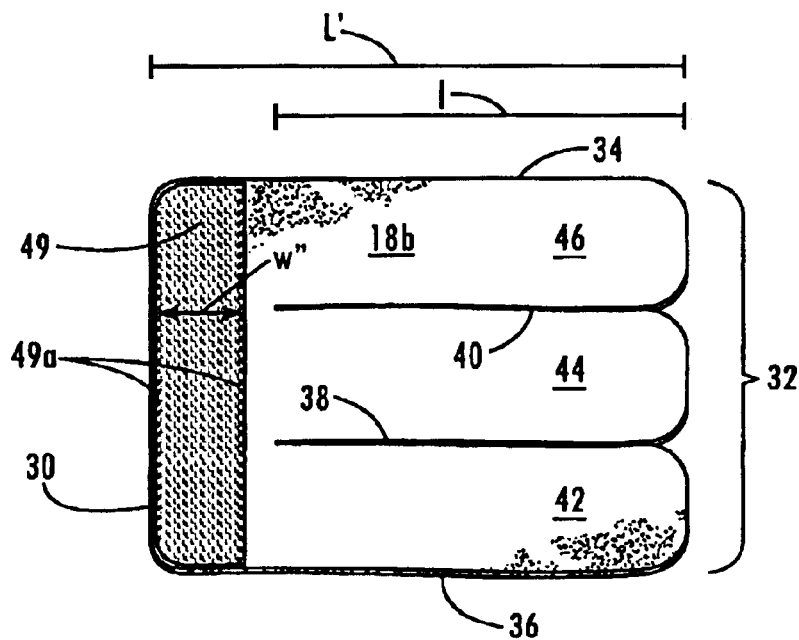
FIG. 5 is a rear plan view of the secondary strap member of FIG. 4.

The strap members 12 and 14 are each preferably of one-piece construction and made of a soft and substantially elastic material. A preferred material is an open-celled, elastomeric, non-latex foam material 18 having a hook-receptive fabric 20 on one surface (FIG. 1a). This provides a foam surface 18a and an opposite fabric surface 20a on the strap member 12, and a foam surface 18b and an opposite fabric surface 20b on the strap member 14. A preferred material of this type is available under the trademark FABRIFOAM from Fabrifoam Products of Exton, Pa. However, virtually any suitable substantially elastic material may be used to provide the strap members 12 and 14. The FABRIFOAM material has a thickness T, with the foam material having a thickness T' and the fabric 20 having a thickness t.

The strap member 12 is crescent-shaped when laid flat, having a longest length L1 and a shortest length L2 defined between opposite ends 22 and 24, and a, substantially constant width W defined between opposite sides 26 and 28. The curvature of the strap member 12 is preferably substantially constant and symmetrical, with the halves on either side of mid-line M of the member 12 being substantially identical. A length of a plastic hook material 29 having a length corresponding to the width W of the strap member 12 and a width w is preferably secured to the foam surface 18a of the strap member 12 adjacent the end 22, as by stitches 29a.

The strap member 14 is preferably substantially rectangular when laid flat, having an overall length L' defined between opposite ends 30 and 32, and a width W' defined between opposite sides 34 and 36. A pair of spaced-apart cuts 38 and 40 extend from the end 32 to points A and B on the strap member 14, respectively, to define individual finger portions 42, 44 and 46. Each of the finger portions 42–46 preferably have a width w' and a length l. The cuts 38 and 40 are preferably substantially aligned to be parallel with one another and with the length axis of the strap member 14. A length of a plastic hook material 49 having a length corresponding to the width W' of the strap member 14 and a width w" is preferably secured to the foam surface 18b of the strap member 14 adjacent the end 32, as by stitches 49a.

The strap member 14 is preferably releasably secured to the strap member 12 as by pressing the hook material 49 against the fabric surface 20a of the strap member 12, preferably substantially along the mid-line M of the member 12. However, it will be understood that the strap member 14 may be located at other locations relative to the strap member 12. Also, the strap member 14 may be secured to the strap member 12 as by non-releasable fasteners, such as by stitches.

For installation of the strap system 10 onto a user, fastening members 50 are provided for releasably securing the fingers 42–46 to the fabric surface 20a of the strap member 12. The fastening members 50 are preferably short lengths of a plastic sheet material having a plurality of hook members defined on one surface thereof of a type commonly used for matingly engaging hook and loop material and which readily engage the fabric surface 20a of the strap member 12 and the fabric surface 20b of the fingers 42–46 of the strap member 14. The purpose of the fastening members 50 is to span between adjacent portions of the strap member 12 and the fingers 42–46 maintain them in a desired orientation. As will be appreciated, tape, adhesive strips or other fasteners could be used as well.

For the purpose of example only, the strap members 12 and 14 may have the following dimensions:

| Reference numeral | Dimension (inches) |
| --- | --- |
| L1 | |
| L2 | 14 |
| L' | 8 |
| I | 6 |
| W | 8 |
| W' | 6 |
| w | 1 |
| w' | 2 |
| w" | 1 |
| T | 5/64 |
| T' | 1/16 |
| t | 1/64 |

However, it will understood that the strap member 12 may be provided in various other dimensions suitable for the purpose.

Figure 6:
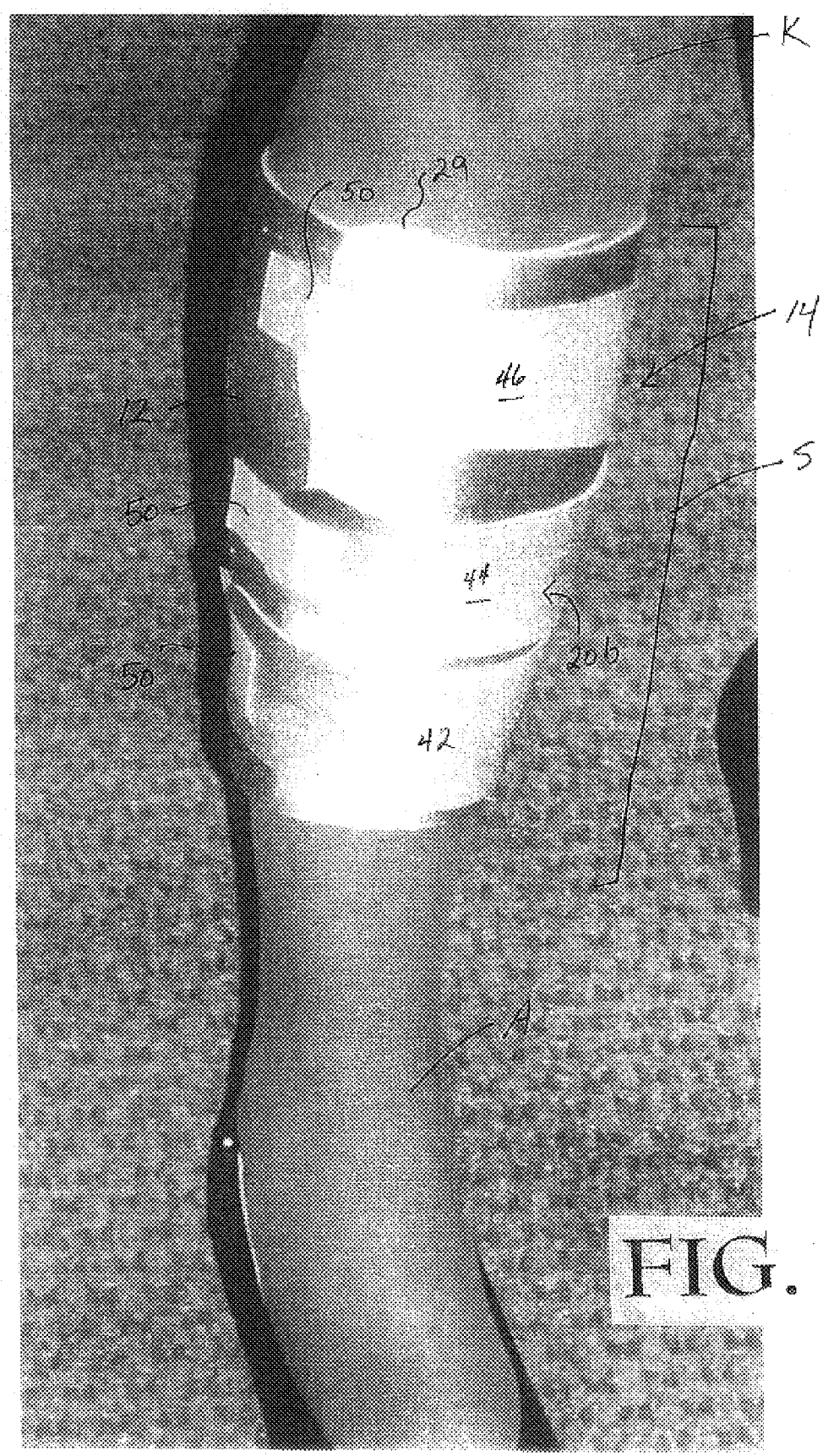
FIG. 6 is a frontal view of the strap system of FIG. 1 installed on a user.
Figure 7:
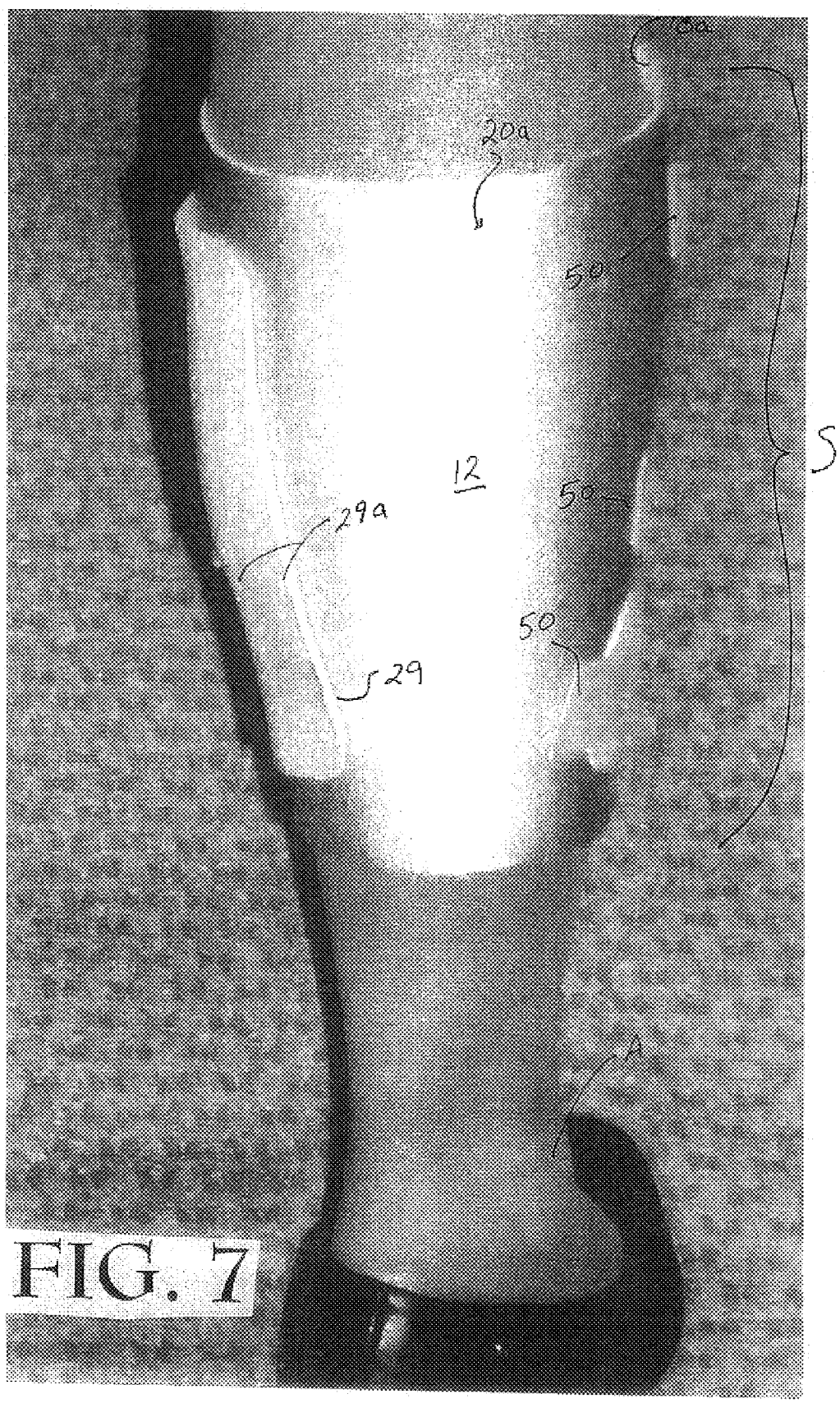
FIG. 7 is a rear view of the strap system of FIG. 1 installed on a user.

Turning now to FIGS. 6–7, there is shown the strap system 10 installed in a preferred manner on a shin S of a user's leg in-between ankle A and knee K. FIG. 6 is a frontal view and FIG. 7 is a rear view. The system 10 is preferably installed as by placing the foam surface 18a against the shin S with the longer side 28 adjacent and below the knee K and the shorter side 26 adjacent and above the ankle A to accommodate the respective larger and smaller dimensions of the calf muscle. The end 24 is preferably held near the front part of the shin and the end 22 pulled to desired tension the strap member 12 about the shin S. The end 22 may then be secured to the outer surface 20a of the strap member by the hook material 29. Next, the fingers 42–46 are preferably individually tensioned in desired directions and secured to discrete locations of the outer fabric surface 20 using the fasteners 50. In a preferred embodiment, the fingers 42–46 are positioned obliquely relative to the leg, each at an angle of from about 25° to about 50°, most preferably from about 30° to about 45° from the horizontal plane. The placement on the leg preferably corresponds to a preferred treatment zone as may be determined by a physician.

The strap system of the invention is intended for use under the direction and supervision of a physician or other appropriate health care provider for treating shin pain and associated conditions such as shin splints. The invention enables a user to conveniently adjust the tension thereof to adjust the amount and direction of the tension applied to portions of the shin.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A device for treating pain in a shin defining a length axis and located between an upper location adjacent a knee and a lower location adjacent an ankle of a user, the device comprising a first substantially elastic and flexible strap member having a pair of opposite ends and an inner surface and an outer surface, the first strap member being substantially crescent shaped and having an upper uniformly bowed arcuate edge and a lower uniformly bowed arcuate edge substantially parallel to the upper uniformly arcuate edge and shorter than the upper uniformly arcuate edge, the first strap member including a first fastener operatively associated with one of the ends of the first strap member and being positionable to be wrapped in a state of tension and generally laterally around the shin of the user so as to be substantially encircling the length axis of the shin with the upper uniformly arcuate edge of the first strap member below the knee and the lower uniformly arcuate edge of the first strap member above the ankle of the user and securable in the state of tension and wrapped configuration by the first fastener, and a second substantially rectangular elastic strap member having a first end releasably securable adjacent the outer surface of the first strap member so as to be adjustably positionable relative to the first strap member and including a plurality of longitudinal cuts defined thereon adjacent a second opposite end thereof to define at least three independently conformable fingers to be independently positioned and tensioned in a direction generally away from the second end and obliquely relative to the leg of the user about the outer surface of the first strap member at an angle of from about 25 degrees to about 50 degrees from a horizontal axis extending substantially normal to the length axis of the shin, and one or more second fasteners associated with each of the fingers for releasably securing the tensioned fingers to the outer surface of the first strap member to maintain the fingers in their tensioned states.

2. The device of claim 1, wherein the first strap member has a fabric covering over foam.

3. The device of claim 1, wherein the second strap member is releasably securable to the first strap member.

4. A method for treating pain of a human shin defining a length axis and located between an upper location adjacent a knee and a lower location adjacent an ankle of a human user, the method comprising the steps of:

providing a strap system including a first substantially elastic and flexible strap member having a pair of opposite ends and an inner surface and an outer surface, the first strap member being substantially crescent shaped and having an upper uniformly bowed arcuate edge and a lower uniformly bowed arcuate edge parallel to the upper uniformly arcuate edge and shorter than the upper uniformly arcuate edge, the first strap member including a first fastener operatively associated with one of the ends of the first strap member and being positionable to be wrapped in a state of tension and generally laterally around the shin of the user with the upper uniformly arcuate edge of the first strap member positionable below the knee and the lower uniformly arcuate edge of the first strap member above the ankle of the user so as to be substantially encircling the length axis of the shin and securable in the state of tension and wrapped configuration by the first fastener, and a second substantially rectangular elastic strap member having a first end releasably securable adjacent the outer surface of the first strap member so as to be adjustably positionable relative to the first strap member and including a plurality of longitudinal cuts defined thereon adjacent a second opposite end thereof to define at least three conformable fingers which are independently positionable and tensionable in a direction generally away from the second end and obliquely relative to the leg of the user about the outer surface of the first strap member, and one or more second fasteners associated with each of the fingers for securing the tensioned fingers to the outer surface of the first strap member; securing the second strap member to the outer surface of the first strap member, independently tensioning each of the fingers of the seconds strap member at an angle of from about 25 degrees to about 50 degrees from a horizontal axis extending substantially normal to the length axis of the shin about the outer surface of the first strap member; and releasably securing the fingers in their tensioned states using the second fasteners to maintain the fingers in their tensioned states.

5. The method of claim 4, wherein the step of securing the second strap member to the outer surface of the first strap member comprises releasably securing the second strap member to the outer surface of the first strap member.

* * * * *